(12) United States Patent
Nishimura et al.

(10) Patent No.: US 7,682,570 B2
(45) Date of Patent: Mar. 23, 2010

(54) MULTIWELL PLATE

(75) Inventors: Akiko Nishimura, Mishima (JP); Takafumi Kajitani, Kawasaki (JP)

(73) Assignee: Research Organization of Information and Systems, Tachikawa-shi (JP)

( * ) Notice: Subject to any disclaimer, the term of this patent is extended or adjusted under 35 U.S.C. 154(b) by 457 days.

(21) Appl. No.: 10/581,493

(22) PCT Filed: Dec. 3, 2004

(86) PCT No.: PCT/JP2004/018454

§ 371 (c)(1),
(2), (4) Date: Mar. 26, 2007

(87) PCT Pub. No.: WO2005/059090

PCT Pub. Date: Jun. 30, 2005

(65) Prior Publication Data

US 2007/0258863 A1 Nov. 8, 2007

(30) Foreign Application Priority Data

Dec. 3, 2003 (JP) ............................. 2003-405263
Feb. 25, 2004 (JP) ............................. 2004-050541

(51) Int. Cl.
*B01L 3/00* (2006.01)
*C12M 3/00* (2006.01)

(52) U.S. Cl. ................. 422/102; 435/288.4; 435/305.2; 435/305.3; 435/305.4; 435/307.1

(58) Field of Classification Search ................. 422/102; 435/288.4, 305.2–305.4, 307.1
See application file for complete search history.

(56) References Cited

U.S. PATENT DOCUMENTS 5,096,676 A * 3/1992 McPherson et al. ......... 117/206
5,958,675 A * 9/1999 Wicks et al. ................... 435/5

FOREIGN PATENT DOCUMENTS

| JP | 63-109780 A | 5/1988 |
| JP | 7-111887 A | 5/1995 |
| JP | 9-206062 A | 8/1997 |
| JP | 10-257887 A | 9/1998 |
| JP | 2002-159284 A | 6/2002 |
| JP | 2002-218967 A | 8/2002 |
| JP | 2005-118013 A | 5/2005 |

* cited by examiner

*Primary Examiner*—Brian R Gordon
*Assistant Examiner*—Shogo Sasaki
(74) *Attorney, Agent, or Firm*—Birch, Stewart, Kolasch & Birch, LLP

(57) ABSTRACT

A thin multiwell plate for use in the transportation of microbes, animal cells, DNA, etc. The multiwell plate of the present invention comprises a sheet laminate, wherein the laminate has multiple hollow parts in which a water adsorbent material is retained. A multiplicity of microbe samples, etc. can be transported conveniently and safely by causing the water adsorbent material to retain a microbe-containing solution, a DNA sample solution, etc. In particular, an ultrathin multiwell plate can be provided due to construction with a sheet laminate, thereby rendering the transportation thereof extremely easy.

5 Claims, 3 Drawing Sheets

MULTIWELL PLATE

TECHNICAL FIELD

The present invention relates to a multiwell plate, particularly a thin multiwell plate useful for carrying and storing microbes (strains), phages, DNA, cells, etc.

BACKGROUND ART

Conventionally, materials produced by microbes have been used as a source of new medical development. Explorations have been made to seek such microbes producing useful materials.

Further, useful materials have been produced by culturing microbes introduced genes for cording useful materials (transformant) by using recent genetic recombination technologies.

In addition, in the food industry, a variety of foods have been manufactured by fermentation using microbes. Thus, in the fields of medicine, biochemistry, food, chemistry, etc., microbes play an important role and are kept carefully because clone microbes are valuable sources. Generally, these microbes are stored by a stab culture method, a freezing method, a freeze-drying method, etc.

Research institutions storing the above-mentioned microbes carry the microbes when they are asked to supply the microbes by other research institutions.

Usually, Transportation of microbes is carried out by spotting a culture solution of microbes to paper filter and wrapping with packaging wraps, or containing in ampoule. In case of a large number of microbes, the culture solution is dividedly poured into a micro-titer plate and sealed with a vinyl sheet or spot inoculated in agar medium.

Known multiwell plates for use of microbes are referred to Japanese Patent Unexamined Publication No. 2001-218575 and Japanese Patent Unexamined Publication No. 2002-199874.

However, the above-mentioned methods for carrying microbes absorbed with filer papers have problems of contamination and are ineffective because the number of paper filters increases in case of large number of microbes.

With regard to the methods of micro-titer plate, agar medium or ampoule transportation, there is a problem of container breakage, which further causes a problem of microbe contamination, and also there is a problem of bulky.

In order to solve the above-mentioned problems, the applicants of the present application proposed a thin multiwell plate (Japanese Patent Application 2003-359534). This multiwell plate is superior enough to achieve the object. However, this multiwell plate requires to be replicated by inverting to contact with a culture medium and the like when they are used. For this reason, a position relation between strains on the multiwell plate and replicated strains on the culture medium is a mirror relation and there was a possibility of misidentifying the positions of the strains.

The present invention to solve the problems provides a thin multiwell plate which simply and safely carries and stores a number of microbes and which is devised in such that the position of multiwell plate corresponds to that of replicated ones.

DISCLOSURE OF THE INVENTION

A multiwell plate of the present invention comprises a laminated body of sheets which has plural hollow portions, each of which hold a water adsorbent material.

Preferable embodiments of the invention are described.

A multiwell plate comprises:
(a) a bottom sheet;
(b) a removal sheet adhered on the bottom sheet and having plural through-holes;
(c) a spacer sheet adhered on the removal sheet, having through-holes whose diameter is substantially same with the through-hole of the removal sheet and which are corresponding to the position of the through-holes of the removal sheet;
(d) a water adsorbent material fixing sheet adhered on the spacer sheet, having through-holes whose diameter is smaller than the through-hole of the spacer sheet, and which are corresponding to the position of the through-holes of the spacer sheet; and
(e) a coversheet covering a top of the water adsorbent material fixing sheet;
wherein the bottom sheet, the removal sheet, the spacer sheet, the water adsorbent material fixing sheet and the coversheet are sequentially laminated, and the water adsorbent material is held in each through-hole of the spacer sheet by being adhered by the water adsorbent material fixing sheet.

A multiwell plate comprises:
(a) a bottom sheet;
(b) a removal sheet adhered on the bottom sheet, and having plural through-holes;
(c) an auxiliary sheet adhered on the removal sheet, and having through-holes whose diameter is substantially same with the through-hole of the removal sheet and which are corresponding to the position of the through-holes of the removal sheet;
(d) a spacer sheet adhered on the auxiliary sheet, and having through-holes whose diameter is larger than the through-holes of the auxiliary sheet and which are corresponding to the position of the through-holes of the auxiliary sheet;
(e) a water adsorbent material fixing sheet adhered on the spacer sheet, and having through-holes whose diameter is smaller than the through-holes of the spacer sheet and which are corresponding to the position of the through-holes of the spacer sheet;
(f) a coversheet covering a top of the water adsorbent material fixing sheet;
wherein the bottom sheet, the removal sheet, the auxiliary sheet, the spacer sheet, the water adsorbent material fixing sheet and the coversheet are sequentially laminated, and the water adsorbent material is held in each through-hole of the spacer sheet by being adhered by the water adsorbent material fixing sheet.

Another embodiment is depicted in FIG. 4. A multiwell plate comprising: a body of laminated sheets and water adsorbent materials, wherein said body has plural hollow portions, each of which holds one of said water adsorbent materials, wherein said body of laminated sheets comprises, (a) a bottom sheet; (b) a first spacer sheet having plural through-holes, in which each of said through-holes has a smaller diameter on a first face of said first spacer sheet and a larger diameter on a second face defining a stepped side wall within each of said through-holes, wherein said bottom sheet is adhered to said first face of said first spacer sheet; (c) a second spacer sheet having plural through-holes, in which each of said through-holes has a smaller diameter on a first face of said second spacer sheet and a larger diameter on a second face defining a stepped side wall within each of said through-holes, wherein said second face of said second spacer sheet is adhered to said second face of said first spacer sheet, further wherein said through-holes of said first and second spacer sheet overlap with respect to each other; and (d) a coversheet covering said first face of said second spacer sheet; wherein said water adsorbent materials having diameters larger than the smaller diameter of said through-holes is sandwiched between said spacer sheets.

Further, it is preferable that the multiwell plate of the invention is sealed inside a packing container.

The above-mentioned multiwell plate is ultra thin and, entire thickness is no more than 3 mm, preferably, no more than 1 mm. And it may be no more than 0.5 mm depending on material selection.

BEST MODE FOR CARRYING OUT THE INVENTION

The present invention will be described in detail hereinafter with reference to drawings, but the invention is not to be limited to these examples.

Figure 1:
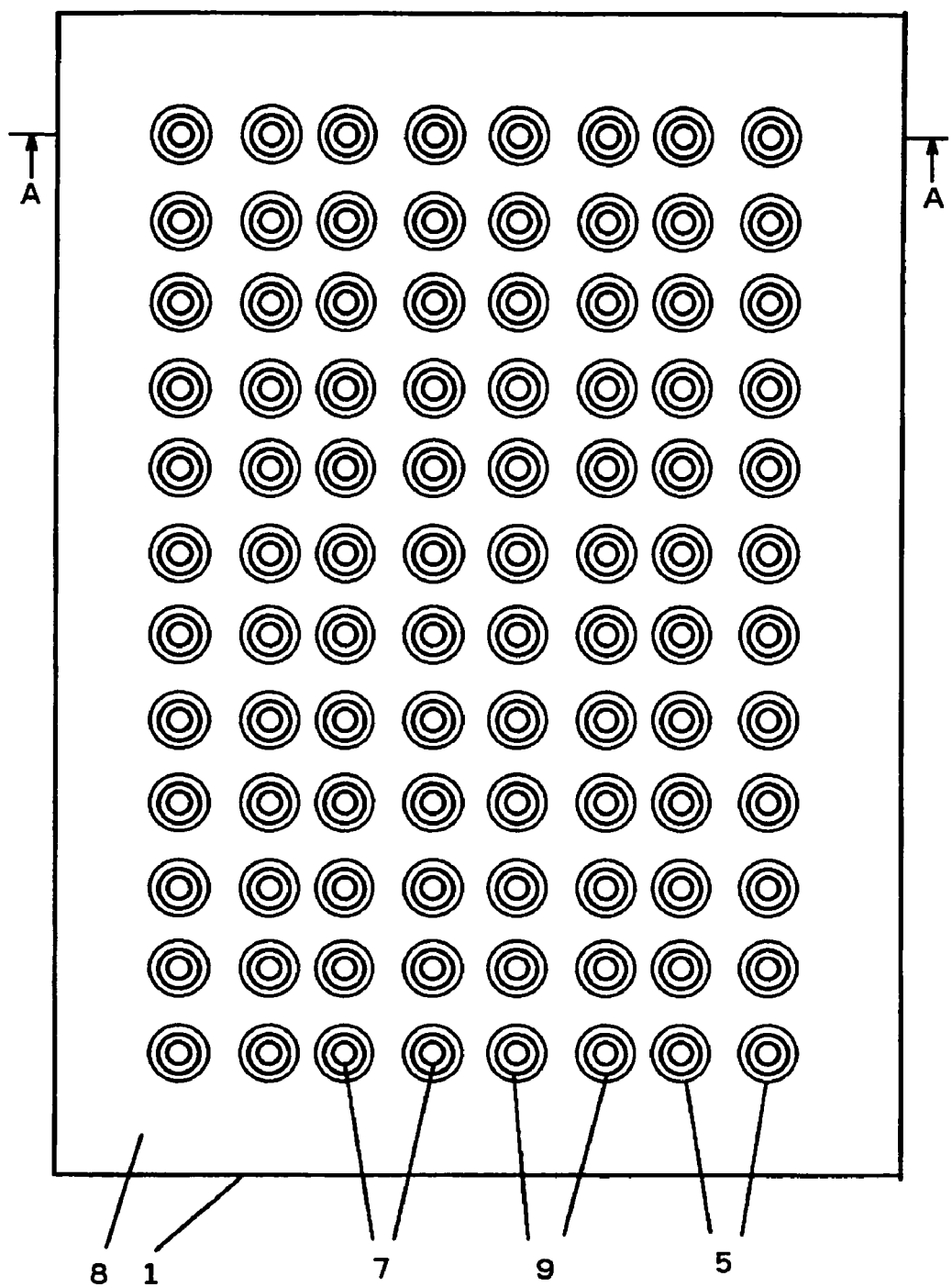
FIG. 1 is a plane schematic view showing an example of the multiwell plate related to the invention.
Figure 2:
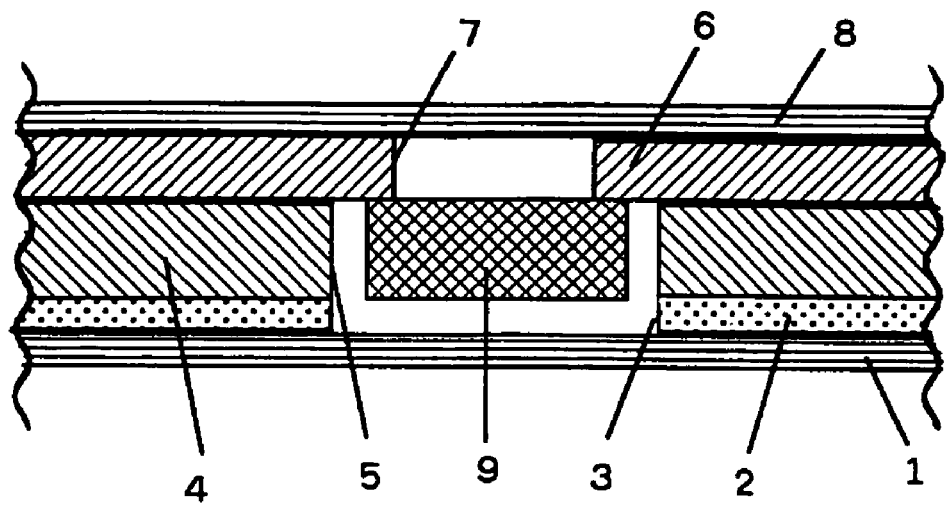
FIG. 2 is a partially enlarged schematic view showing the end view taken in the line A-A of FIG. 1.

FIGS. 1 and 2 show an example of the multiwell plate related to the invention. FIG. 1 is a plane schematic view and FIG. 2 is a partially enlarged end section schematic view of the line A-A of FIG. 1. In FIGS. 1 and 2, 1 refers to a bottom sheet, 2 is a removal sheet, 3, 5 and 7 are through-holes, 4 is a spacer sheet, 6 is a water adsorbent material fixing sheet, 8 is a coversheet, 9 is a water adsorbent material.

FIGS. 1 and 2 show the multiwell plate comprising 96 pieces of wells as an example of the invention. The number of the wells is not limited to 96 but the appropriate number may be as desired. For example, 6, 12, 24, 48, 384 are exemplified (same as in examples hereinafter).

And in a concept of the present specification, a sheet contains a film.

In FIGS. 1 and 2, the bottom sheet 1 is made of water-resist material, preferably plastic material, for example, PET (polyethylene terephthalate), silicone resin, PE (polyethylene), PP (polypropylene), PS (polystyrene), etc. Materials having a cohesive property are especially preferable.

Thickness of the bottom sheet 1 is not specifically limited but a strength to hold the removal sheet 2 may be satisfied. Generally, a sheet with thickness of about 50 to 100 μm is used.

An upper surface of the bottom sheet 1 is covered with removable adhesive and the removal sheet 2 is adhered through this adhesive layer (not shown in figures, same hereinafter). In case that the bottom 1 is made of material having a cohesive property, the above adhesive is not needed to use. Total 96 pieces of the through-holes 3 arranged in 8 pieces×12 columns are formed on the removal sheet 2.

The through-hole 3 is cylindrical and a diameter of the hole is generally about 5 mm which is not limited to. The shape of the through-hole 3 is generally cylindrical but it is not limit to this shape but the cross section of the hole may be rectangular. The through-holes 3 mentioned above and the through-holes 5 described later are provided to form a well and the number of the hole is not limited to 96.

Material of the removal sheet 2 is not specifically limited, but easily removable material is preferable. Generally fluorinated resin sheet is used. Thickness of the removal sheet is not specifically limited. Generally the thickness is about 30 to 70 μm and 50 μm is preferable.

As for the removal sheet 2, a removal sheet supported by plastic material which is commercially available may be used.

The spacer sheet 4 is adhered on an upper surface of the removal sheet 2 through an adhesive layer. The spacer sheet 4 is provided with the through-hole 5 in such way that the through-hole 5 is corresponding to the through-hole 3 of the removal sheet 2 in the position and substantially same with the through-hole 3 in diameter.

The spacer sheet 4 is made of water-resist material, preferably plastic material, for example, PET, silicone resin, PE, PE, PS, etc.

Thickness of the spacer sheet 4 is substantially same as that of the water adsorbent material 9 described later. Generally a sheet of about 100 to 1000 μm, or preferably about 150 to 400 μm is used.

An upper surface of the spacer sheet 4 adhered with the water adsorbent material fixing sheet 6 through an adhesive layer. The water adsorbent material fixing sheet 6 is provided with the through-hole 7 in such way that the through-hole 7 is corresponding to the through-hole 5 of the spacer sheet 4 in the position and is slightly smaller than the through-hole 5 in diameter.

The water adsorbent material fixing sheet 6 is made of water-resist material, preferably plastic material, for example PET, silicone resin, PE, PP, PS, etc.

Thickness of the water adsorbent material fixing sheet 6 to support the water adsorbent material 9 described later may be satisfied. Generally a sheet of about 50 to 1000 μm, preferably about 80 to 400 μm, more preferably 150 to 180 μm is used.

An upper surface of the water adsorbent material fixing sheet 6 is entirely covered with the coversheet 8. Used is the cover sheet 8 having the same material and thickness with those of the bottom sheet 1, and preferable is having a cohesive property.

A hollow portion of the sheet lamination comprises the bottom sheet 1, the through-holes 3, 5 and 7 and the coversheet 8.

The water adsorbent material 9 is contained in the through-hole 5 of the spacer sheet 4. The water adsorbent material 9 is supported by being adhered to the water adsorbent material fixing sheet 6 on the circumference of the upper surface thereof.

Material of the water adsorbent material 9 is not specifically limited as long as it permeates and holds subjects to be carried (e.g. solution containing microbes), but preferably fiber material, for example, paper filter, unwoven fabric, felt, etc.

A shape of the water adsorbent material 9 may be any shape to conform to that of the through-hole 5. In case of the through-holes 3 and 5 having a diameter of 5 mm as mentioned above, the diameter of the water adsorbent material 9 is prepared to be 3 mm.

Preparation of the multiwell plate of the invention having the above mentioned construction, comprises steps of adhering the water adsorbent material fixing sheet 6 to the coversheet 8, adhering the spacer sheet 4 to the water adsorbent material fixing sheet 6, filling the water adsorbent material 9 in each through hole 5 to adhere to the water adsorbent material fixing sheet 6 under pressing, sequentially adhering the removal sheet 2 and the bottom sheet 1, and inverting the entire portion.

Figure 3:
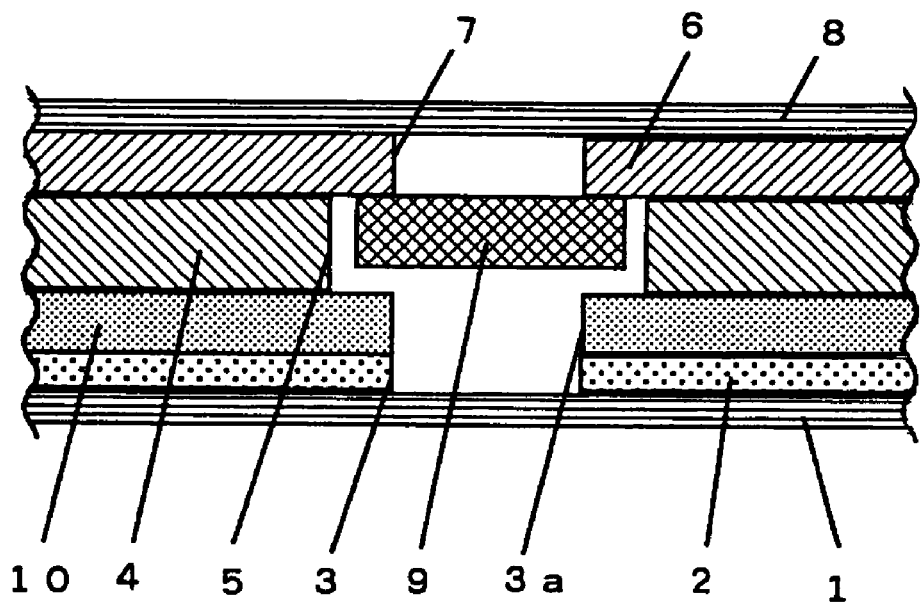
FIG. 3 is a partially enlarged end section schematic view showing a modification embodiment of the multiwell plate related to the invention.

FIG. 3 shows a modified embodiment of the multiwell plate shown in FIGS. 1 and 2 and same reference numerals are used for the same members.

In this embodiment, an auxiliary sheet 10 is sandwiched between the spacer sheet 4 and the removal sheet 2. The auxiliary sheet 10 is provided with a through-hole 3a in such way that the through-hole 3a is corresponding to the through-hole 7 of the water absorbent material fixing sheet 6 in the position and substantially same or smaller than the through-hole 7 in diameter. The diameter of the through-hole 3 provided in the removal sheet 2 is also substantially same with the through-hole 3a. An example as material of the auxiliary sheet 10 is similar material of the water adsorbent material fixing sheet 6. The thickness of the auxiliary sheet 10 is not specifically limited appropriate thickness is used.

The auxiliary sheet 10 is provided to prevent the water adsorbent material 9 permeated with a microbe-containing solution from falling on the bottom sheet 1 in the usage of the multiwell plate related to the invention described later. The water adsorbent material 9 dropped on the bottom sheet 1 causes problems that the water adsorbent material 9 falls off the multiwell plate at the step of separating the bottom sheet 1 in use.

Figure 4:
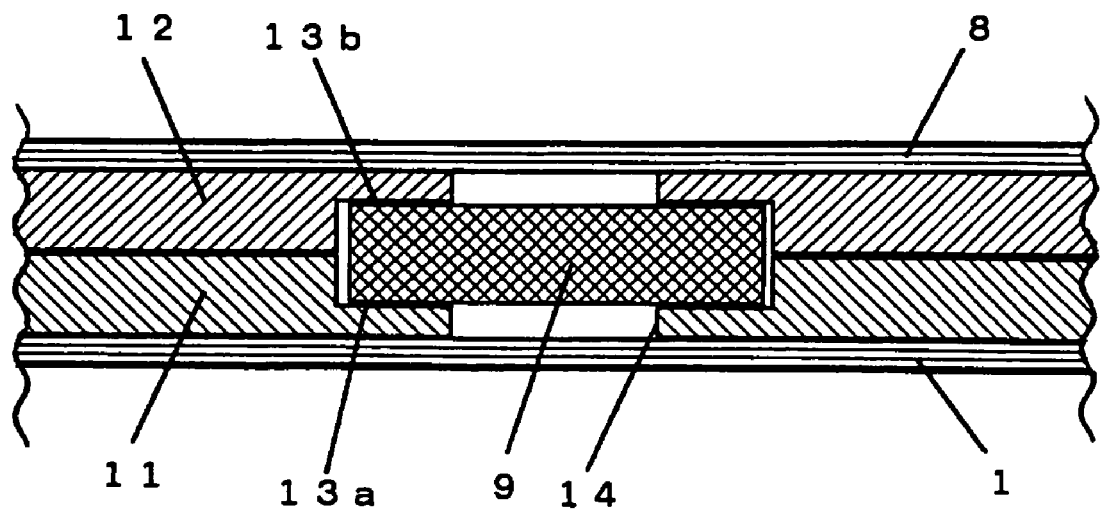
FIG. 4 is a partially enlarged end section schematic view showing another example of the multiwell plate related to the invention.

FIG. 4 shows another embodiment of the multiwell plate related to the invention. FIG. 4 is an enlarged end section schematic view showing a multiwell plate having the similar appearance with the multiwell plates shown in FIG. 1. Same reference numerals are used for the same members of the multiwell plates shown in FIGS. 1 and 2.

In the multiwell plate of this embodiment, a bottom sheet 1, spacer sheets 11 and 12 having plural through-holes and a cover sheet 8 are sequentially laminated. Each through-hole of the spacer sheets 11 and 12 is provided with holding means 13a and 13b for holding the water adsorbent material 9 which is held in each through-hole 14 by the holding means.

The similar materials of the multiwell plates shown in FIGS. 1 and 2 are used for the bottom sheet 1, the spacer sheets 11 and 12, the water adsorbent material 9 and the coversheet 8.

More specifically, the lower spacer sheet 11 and the upper spacer sheet 12 which have plural through-holes 14 are sequentially adhered on the bottom sheet 1. The lower spacer sheet 11 and the upper spacer sheet 12 are provided with a pair of notch concave portions 13a and 13b along the circumference of through-hole 14 and end portion of the water adsorbent material 9 is engaged in and held by the concave portions 13a and 13b. That means, the concave portions 13a and 13b constitute a holding means for the water adsorbent materials 9. In the above embodiment, the concave portions 13a and 13b function as the holding means for the water adsorbent material 9. However the water adsorbent material 9 may be held in the spacer sheets 11 and 12 by adhering side surfaces of the water adsorbent material 9 instead.

Specifically, FIG. 4 shows a multiwell plate comprising: a body of laminated sheets and water adsorbent materials, wherein said body has plural hollow portions, each of which holds one of said water adsorbent materials, wherein said body of laminated sheets comprises, (a) a bottom sheet; (b) a first spacer sheet having plural through-holes, in which each of said through-holes has a smaller diameter on a first face of said first spacer sheet and a larger diameter on a second face defining a stepped side wall within each of said through-holes, wherein said bottom sheet is adhered to said first face of said first spacer sheet; (c) a second spacer sheet having plural through-holes, in which each of said through-holes has a smaller diameter on a first face of said second spacer sheet and a larger diameter on a second face defining a stepped side wall within each of said through-holes, wherein said second face of said second spacer sheet is adhered to said second face of said first spacer sheet, further wherein said through-holes of said first and second spacer sheet overlap with respect to each other; and (d) a coversheet covering said first face of said second spacer sheet; wherein said water adsorbent materials having diameters larger than the smaller diameter of said through-holes is sandwiched between said spacer sheets.

A preparing method of the multiwell plate shown in FIG. 4, for example, comprises a step of adhering the lower spacer sheet 11 having the notch concave portion 13a in the through-hole 14 to the bottom sheet 1, and then a step of disposing the water adsorbent material 9 in the notch concave portion 13a of each through-hole 14, a step of adhering the upper spacer sheet 12 having the notch concave portion 13b, and a step of covering the top of the upper spacer sheet 12 with the coversheet 8.

The upper spacer sheet 12 and the lower spacer sheet 11 may be fusion bonded by the conventional method including high frequency welding.

The above mentioned multiwell plate of the invention is preferably sealed inside a sealable container (e.g. plastic bag, plastic container, etc.). As a container, a plastic bag is preferable due to simplicity.

Usage of the multiwell plate of the invention is described hereinafter by referring to the multiwell plate shown in FIGS. 1 and 2 with a microbe-containing solution as a subject to be carried.

The multiwell plate sealed inside the container as mentioned above is sterilized by the conventional means (e.g. electron sterilization, gamma sterilization, high-pressure steam sterilization, etc.). The containers in the state of sterilization are supplied to users.

Users open the container in a clean room, take out the multiwell plate, and remove the coversheet 8.

After opening the upper surface, users drop a microbe-containing solution on the water adsorbent material 9 through the through-hole 7 so that microbes (strains) permeate for preservation.

As for microbe containing solution, generally used is the solution in which microbes cultured and preserved until the stationary phase are dispersed to the conventional medium (e.g. glycerin solution, physiological saline, etc.). Drop amount of the microbe containing solution may be appropriately selected, but generally the amount is about 10 μl.

Because plural of the water adsorbent materials 9 are provided in the multiwell plate of the invention, a variety of microbe types (strains) can be held. That means, with 96-hole-multiwell plate shown in the attached drawing, 96 types of microbes can be held.

After holding microbes each in the water adsorbent material 9, an upper surface of the water adsorbent material fixing sheet 6 is covered with the coversheet 8, thereby preventing from contamination and incorporation between holes.

After covering with the coversheet 8, the multiwell plate is contained in the above-mentioned container (preferably plastic bag), and the opening portion of the container is sealed with the conventional sealing means (e.g. heat seal, sealing chuck, etc.) and the multiwell plate is carried.

The carried multiwell plate of the invention is opened in the clean room by users who received, brought into close contact with a conventional solid medium after the bottom sheet 1 is removed, and replicated on the medium, thereby entire microbes on the plate can be replicated at one time.

Microbes held in the multiwell plates are replicated on the solid medium as they are, so that position relation is clear and misrecognition is prevented. And further influences of the adhesive can prevent because the removal sheet 2 is still attached.

In case that subjects to be carried are DNA samples like samples for PCR, first a conventional multiwell plate with wells which are each filled with a solution (for example, PCR solution in case that the sample is used for PCR) is prepared. Next, the bottom sheet 1 of the multiwell plate of the invention is removed (the removal sheet 2 is also removed if the removal sheet 2 is included), the multiwell plate is brought into contact with the above-mentioned conventional multiwell plate using adhesion power of the adhesive layer existing on the lower surface of the spacer sheet (4 or 11) or the auxiliary sheet 10. In this case, the contact is made so as to correspond with the position of the water adsorbent material 9 with that of each well of the conventional multiwell plate. After this contact, the entire portion is inverted to contact the solution in the well with the water adsorbent material 9 and extract DNA samples in the water adsorbent material 9 into the solution. This state is kept for a while (about 10 minutes). Next, the inversion is repeated again to restore the original state, and the DNA samples in the water adsorbent material 9 are transferred to the solution by conventional means such as centrifugation. And then the multiwell plate is separated and the DNA samples in the well are subjected to the processes including PCR processing by a conventional manner.

In the above-mentioned usage, microbes are not specifically limited but examples are *Escherichia coli, Bacillus subtilis*, yeast, etc. And the microbes may be transformant including recombinant genes and microbes infected with phages having recombinant genes. And further in microbes available of freezing preservation, a microbe-containing solution including appropriate freezing protective agent (e.g. DMSO) is dropped to the water adsorbent material 9 and freezing process may be performed after sealing process as mentioned above. With this embodiment, microbes can be stored in the frozen state.

The multiwell plate of the invention may be used for carrying animal cells as well as microbes. Animal cells generally have anchorage dependency and the water adsorbent material 9 functions as the anchor for the animal cells. Therefore, an animal-cell containing solution is dropped on the water adsorbent material 9 and sealing process is performed as mentioned above, so that the multiwell plate can be used for carrying animal cells. In this case, the freezing protective agent may be added to the animal-cell containing solution to carry or preserve animal cells in the frozen state.

Animal cells may be animal cells including recombinant genes (transformant) as well as the conventional established cell line. Animal cells used for preparation of the transformant include animal cells frequently used in the gene recombination technology, for example, mouse fibroblast C127, Chinese hamster ovary cells CHO, monkey COS cell, etc.

The multiwell plates of the invention shown in FIGS. 3 and 4 may be used substantially same as the above-mentioned way.

INDUSTRIAL APPLICABILITY

With the multiwell plate of the invention, it is remarkably effective because a sheet of plate can carry a number of microbes (or animal cells, DNA samples, etc.), and in addition it can solve the problem of microbe loss and microbe contamination due to breakage of carrying containers. And it dose not take much space because of ultra thin type.

In addition, the plate can be replicated while being contact with the medium in the state that the bottom sheet (removal sheet depending on circumstances) is removed, thereby operation is quite easy and misrecognition of strains position can be prevented because the plate is not required to be inverted.

The most advantageous characteristic that can not be found in the conventional products is that the multiwell plate can be applied directly and easily to PCR amplification and transformation experiment as well as cultivation because the sample is recovered while this multiwell is adhering to the conventional multiwell plate in use.

And because the multiwell plate can be preserved at $-80°$ C. as it is, space is saved. And as for a large amount of sample preservation, it is not required to install a number of ultra-low temperature tanks, and it greatly contributes to the energy saving and the environmental conservation.

EMBODIMENTS

Although the invention is described in details based on Embodiments hereinafter, the invention is not limited to Embodiments.

Embodiment 1

Preparation of the Multiwell Plate Shown in FIGS. 1 and 2

A PE sheet having a cohesive property (manufactured by FSK Co., 85 mm×145 mm×80 μm) was used as a coversheet.

A water adsorbent material fixing sheet made of PET (manufactured by Nitto Seal Co., 85 mm×145 mm×80 μm) having through-holes (about 2 mm diameter) which were arranged at equal space of 8 pieces×12 columns as shown in FIG. 1 was superimposed on and adhered to the coversheet. And then a silicon adhesive (same adhesive is used hereinafter) was evenly applied on the surface of the water adsorbent material fixing sheet.

A spacer sheet made of PET (manufactured by Denka Co., 85 mm×145 mm×150 μm) having through-holes (about 5 mm diameter) in the position corresponding to the holes of the water adsorbent material fixing sheet was superimposed in such that centers of the holes were substantially corresponding to each other and adhered to an adhesive surface of the water adsorbent material fixing sheet. And then paper filter (about 3 mm diameter, about 150 μm thickness) was put in each hole of the spacer sheet and the paper filter was adhered to the water adsorbent material fixing sheet by pressing force. Further, adhesive was applied on the surface of the spacer sheet.

A removal sheet made of fluorinated resin (85 mm×145 mm×50 μm) having through-holes (about 5 mm diameter) in the position corresponding to the holes of the spacer sheet was superimposed in such that centers of these holes were corresponding to each other and adhered to an adhesive surface of the spacer sheet.

As a bottom sheet, the same sheet with the coversheet was used and the sheet was entirely superimposed on and adhered to the removal sheet.

Next, the above lamination body was inverted to produce the multiwell plate of the invention shown in FIGS. 1 and 2.

The obtained multiwell plate was contained in a plastic bag (220 mm×95 mm) and an electronic sterilization process was performed after heat-sealing an opening portion of the bag.

Embodiment 2

Preparation of the Multiwell Plate Shown in FIG. 3

A sheet made of PE having a cohesive property (manufactured by FSK Co., 85 mm×145 mm×80 μm) was used as a coversheet.

A water adsorbent material fixing sheet made of PET (manufactured by Nitto Seal Co., 85 mm×145 mm×180 μm) having through-holes (about 3 mm diameter) which were arranged at equal space of 8 pieces×12 columns was superimposed on and adhered to the coversheet. And then a silicon adhesive was evenly applied on the surface of the water adsorbent material fixing sheet.

A spacer sheet made of PET (manufactured by Denka Co., 85 mm×145 mm×400 μm) having through-holes (about 4.2 mm diameter) in the position corresponding to the holes of the water adsorbent material fixing sheet was superimposed in such that centers of the holes were substantially corresponding to each other and adhered to an adhesive surface of the water adsorbent material fixing sheet. Paper filter (about 4 mm diameter, about 360 μm thickness) was put in each hole of the spacer sheet and the paper filter was adhered to the water adsorbent material fixing sheet by pressing force. Further, adhesive was applied on the surface of the spacer sheet.

An auxiliary sheet made of PET (manufactured by Nitto Seal Co., 85 mm×145 mm×180 μm) having through-holes (about 3 mm diameter) in the position corresponding to the holes of the spacer sheet was superimposed on and adhered to an adhesive surface of the spacer sheet. And then adhesive was applied on the surface of the auxiliary sheet.

A removal sheet made of fluorinated resin (85 mm×145 mm×50 μm) having through-holes (about 3 mm diameter) in the position corresponding to the holes of the auxiliary sheet was superimposed in such that centers of these holes were corresponding to each other and adhered to the adhesive surface of the auxiliary sheet.

As a bottom sheet, the same sheet with the coversheet was used and the sheet was entirely superimposed on and adhered to the removal sheet.

Next, the above lamination body was inverted to produce the multiwell plate of the invention shown in FIG. 3.

The obtained multiwell plate was contained in a plastic bag (220 mm×95 mm) and an electronic sterilization process was performed after heat-sealing an opening portion of the bag.

Embodiment 3

Preparation of the Multiwell Plate Shown in FIG. 4

A PE sheet having a cohesive property (manufactured by FSK Co., 85 mm×145 mm×80 μm) was used as a bottom sheet.

A lower spacer sheet made of PET (manufactured by Nitto Seal Co., 85 mm×145 mm×380 μm) having through-holes (about 3 mm diameter) which were arranged at equal space of 8 pieces×12 columns was superimposed on and adhered to the bottom sheet. A notch concave portion (0.6 mm width, 200 μm height) was provided in each hole of the spacer sheet along circumference of the hole.

Next, paper filter (4 mm diameter, 360 μm) was put in the notch concave portion, and then an upper spacer sheet having similar notch concave portions and made of similar material to those of the lower spacer sheet was adhered to the notch concave portion of each hole. Further the multiwell plate of the invention shown in FIG. 4 was prepared by covering with a coversheet made of the same material as the bottom sheet.

The obtained multiwell plate was contained in a plastic bag (220 mm×95 mm) and an electronic sterilization process was performed after heat-sealing an opening portion of the bag.

What is claimed is:

1. A multiwell plate comprising:
    a body of laminated sheets and water adsorbent materials, wherein said body has plural hollow portions, each of which holds one of said water adsorbent materials,
    wherein said body of laminated sheets comprises,
    (a) a bottom sheet;
    (b) a removal sheet adhered on said bottom sheet and having plural through-holes;
    (c) a spacer sheet adhered on said removal sheet, having matching through-holes, wherein said through-holes of said removal sheet and said matching through-holes of said spacer sheet overlap with respect to each other,
    (d) a water adsorbent material fixing sheet adhered on said spacer sheet, having matching through-holes whose diameter is smaller than said through-holes of said spacer sheet, wherein said through-holes of said removal sheet and said spacer sheet; and said matching through-holes of said water adsorbent fixing sheet overlap with respect to each other, and further wherein said water adsorbent materials having diameters larger than the diameter of said through-holes of said water adsorbent material fixing sheet is adhered to said water adsorbent material fixing sheet and covers said through-holes of said water adsorbent material fixing sheet; and
    (e) a coversheet covering said water adsorbent material fixing sheet.

2. The multiwell plate according to claim 1, wherein the diameter of said through-holes of said removal sheet is substantially same as the diameter of said matching through-hole of said spacer sheet.

3. The multiwell plate according to claim 1, further comprising an auxiliary sheet adhered between said removal sheet and said spacer sheet, and having through-holes which overlap the through-holes of said removal sheet, said spacer sheet and said water adsorbent material fixing sheet.

4. A multiwell plate comprising:
    a body of laminated sheets and water adsorbent materials, wherein said body has plural hollow portions, each of which holds one of said water adsorbent materials,
    wherein said body of laminated sheets comprises,
    (a) a bottom sheet;
    (b) a first spacer sheet having plural through-holes, in which each of said through-holes has a smaller diameter on a first face of said first spacer sheet and a larger diameter on a second face defining a stepped side wall within each of said through-holes, wherein said bottom sheet is adhered to said first face of said first spacer sheet;
    (c) a second spacer sheet having plural through-holes, in which each of said through-holes has a smaller diameter on a first face of said second spacer sheet and a larger diameter on a second face defining a stepped side wall within each of said through-holes, wherein said second face of said second spacer sheet is adhered to said second face of said first spacer sheet, further wherein said through-holes of said first and second spacer sheet overlap with respect to each other; and
    (d) a coversheet covering said first face of said second spacer sheet;
    wherein said water adsorbent materials having diameters larger than the smaller diameter of said through-holes is sandwiched between said spacer sheets.

5. The multiwell plate according to claim 1, 2, 3, or 4 further comprising a packaging container which encases and seals said multiwell plate.

* * * * *